US006362179B1

(12) United States Patent
Nishi et al.

(10) Patent No.: US 6,362,179 B1
(45) Date of Patent: Mar. 26, 2002

(54) SALTS OF AN OPTICALLY-ACTIVE SULFOXIDE DERIVATIVE

(75) Inventors: Takahide Nishi, Tokyo; Takeshi Yamaguchi, Ushiku, both of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/447,401

(22) Filed: Nov. 23, 1999

Related U.S. Application Data

(63) Continuation of application No. PCT/JP98/02308, filed on May 27, 1998.

(30) Foreign Application Priority Data

May 30, 1997 (JP) .............................................. 9-141805

(51) Int. Cl.$^7$ ................... A61K 31/5377; C07D 495/10
(52) U.S. Cl. ..................................... 514/233.5; 544/130
(58) Field of Search ........................ 514/235.5; 544/130

(56) References Cited

U.S. PATENT DOCUMENTS 5,641,777 A   6/1997  Edmonds-Alt et al. .. 514/235.5
6,159,967 A  12/2000  Nishi et al. ............... 514/233.5

FOREIGN PATENT DOCUMENTS

| EP | 0 776 893 A | 6/1997 |
| WO | WO 94/17405 | 8/1994 |
| WO | WO 94/26735 | 11/1994 |
| WO | WO 94/29309 | 12/1994 |
| WO | WO 95/28389 | 10/1995 |

*Primary Examiner*—Fiona T. Powers
(74) *Attorney, Agent, or Firm*—Frishauf, Holtz, Goodman, Langer & Chick, P.C.

(57) ABSTRACT

Hydrochloride of fumarate of 1-{2-[(2R)-(3,4-dichlorophenyl)-4-(3,4,5-trimethyoxybenzoyl)morpholin-2-yl]ethyl}spiro[benzo(c)thiophene-1(3H),4'-piperidin]-(2S)-oxide. These compounds have good oral adsorption and exhibit markedly excellent antagonistic action against both $NK_1$ receptors and $NK_2$ receptors. These compounds are useful as an active ingredient in pharmaceutical compositions for administering to patients for treatment of tachykinin-medicated diseases.

27 Claims, No Drawings

SALTS OF AN OPTICALLY-ACTIVE SULFOXIDE DERIVATIVE

This application is a continuation application of International Application PCT/JP98/02308 filed May 27, 1998.

The present invention relates to novel salts of an optically active sulfoxide derivative having excellent antagonistic activity against both substance P receptors and neurokinin A receptors.

BACKGROUND OF THE INVENTION

Although not very many reports have been made on a low-molecular-weight, non-peptide type compound having antagonistic activity against both substance P receptors ($NK_1$ receptors) and neurokinin A receptors ($NK_2$ receptors), for example, the below-described compounds A, B and C are known as such compounds. According to the specification of PCT publication No. WO 94/17045, the compound B has antagonistic activity against both $NK_1$ and $NK_2$ receptors. A pharmacological test of the compound B made by the present inventors, however, has revealed that the antagonistic activity of the compound B against $NK_1$ receptors in vitro was markedly weak. In addition, when all of these compounds are orally administered, these are accompanied by problems such as insufficient antagonistic activity against both $NK_1$ receptors and $NK_2$ receptors.

Compound A

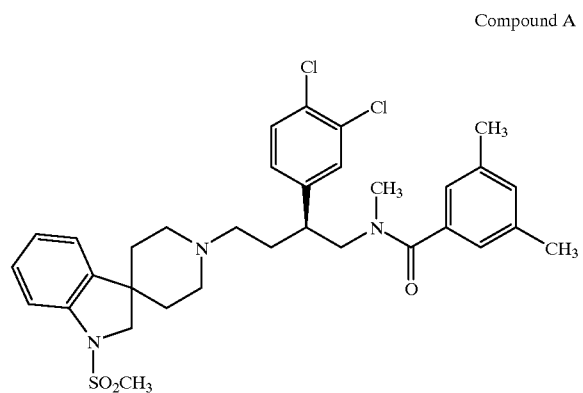

WO 9429309 (1994)

Compound B

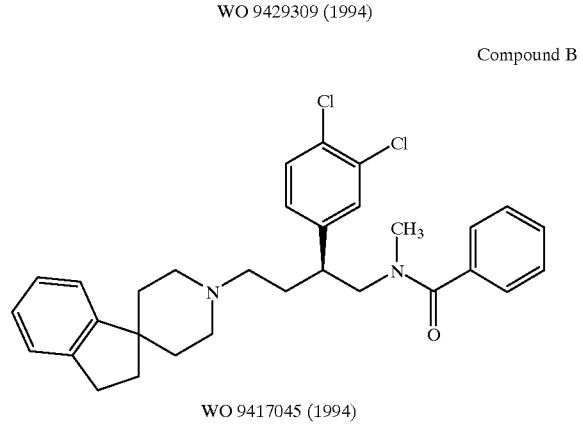

WO 9417045 (1994)

Compound C

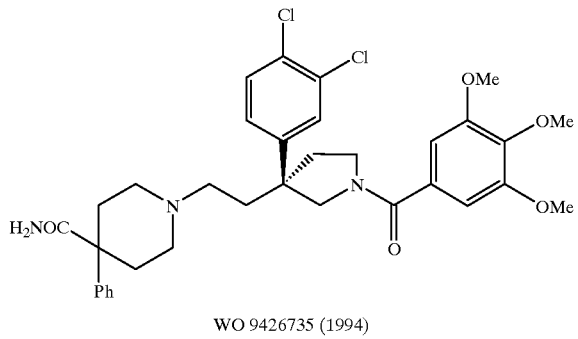

WO 9426735 (1994)

SUMMARY OF THE INVENTION

For a long time, the present inventors have carried out an extensive investigation on the synthesis of derivatives having antagonistic activity against tachykinin (particularly, antagonism against substance P, antagonistic activity against neurokinins A and B) and their pharmacological activity. As a result, it has been found that compared with the above-described known compounds, specific novel salts of an optically active substance of spiro[benzo[c]thiophene-1 (3H),4'-piperidin]-2-oxide having an absolute configuration of S exhibit better oral absorption and excellent antagonistic activity against both $NK_1$ and $NK_2$ receptors to complete the present invention.

An object of the present invention is to provide the above-described compound. Another object of the present invention is to provide a medicament comprising the above-described compound as an effective ingredient, particularly, as a preventive agent or remedy (a composition for prophylaxis or treatment) for tachykinin-mediated diseases. A further object of the present invention is to provide a use of the above-described compound for the preparation of a medicament, particularly, a preventive agent or remedy (a composition for the prevention or treatment) of tachykinin-mediated diseases or is to provide a method for preventing or treating tachykinin-mediated diseases, which comprises administering a pharmacologically effective amount of the compound to a warm-blooded animal.

Examples of the preventive agent or remedy include inhibitors of an $NK_1$ receptor and/or $NK_2$ receptor. Examples of the diseases include diseases of the central nervous system such as anxiety, depression, psychosis and schizophrenia; neurodegenerative diseases such as dementia of AIDS, Alzheimer's senile dementia, Alzheimer's disease, Down's syndrome, demyelinating disease, amyotrophic lateral sclerosis, neuropathy, peripheral neuropathy and neuralgia; respiratory diseases such as chronic obstructive pulmonary disease, bronchitis, pneumonia, bronchoconstriction, asthma and cough; inflammatory diseases such as inflammatory bowel disease (IBD), psoriasis, fibrosis, arthrosteitis, degenerative arthritis and rheumatoid arthritis; eczema; allergies such as rhinitis; hypersensitivity diseases such as hypersensitivity to vines; ophthalmological diseases such as conjunctivitis, vernal conjunctivitis, vernal catarrh, destruction of the blood-aqueous humor barrier caused by various inflammatory eye diseases, elevated introcular pressure and miosis; skin diseases such as contact dermatitis, atopic dermatitis, urticaria and other eczematoid dermatitis; addictions such as alcohol dependency; somatic diseases caused by stress; sympathetic reflex dystrophy such as hand and shoulder syndrome; dysthymia; undesirable immune reactions such as rejection of grafts; diseases relating to immunopotentiation such as systemic lupus erythematosus or immunosuppression; digestive diseases such as diseases caused by abnormalities in nerves regulating the organs, colitis, ulcerative colitis and Crohn's disease; emesis such as emesis induced by adverse effects of X-ray irradiation and chemotherapy, poisons, toxins, pregnancy, vestibular disorders, postoperative illness, gastrointestinal occlusion, reduced gastrointestinal movement, visceral pain, migraine headache, increased intracranial pressure, reduced intracranial pressure or adverse reaction induced by administration of various medicaments; urinary bladder functional diseases such as cystitis and urinary incontinence; eosinophilia caused by collagen diseases, scleriasis or Fasciola hepatica infection; diseases caused by abnormal blood flow due to vasodilation or vasoconstriction such as angina pectoris, migraine headache and Reynauds's disease; and pain of pain nociceptive reception such as migraine headache, headache and toothache.

The novel salts of an optically active sulfoxide derivative according to the present invention are the hydrochloride and fumarate of 1-{2-[(2R)-(3,4 -dichlorophenyl)-4-(3,4,5-trimethoxybenzoyl)morpholin-2-yl]ethyl}spiro[benzo(c)thiophene-1(3H),4'-piperidin]-(2S)oxide.

A novel medicament according to the present invention comprises a compound selected from the above-described ones as an active ingredient;

a novel preventive agent or remedy for tachykinin-mediated diseases according to the present invention comprises a compound selected from the above-described ones as an active ingredient, a novel inhibitor of an $NK_1$ receptor and/or an $NK_2$ receptor according to the present invention comprises a compound selected from the above-described ones as an active ingredient, a novel preventive agent or remedy for asthma and/or bronchitis according to the present invention comprises a compound selected from the above-described ones as an active ingredient, a novel preventive agent or remedy for rhinitis according to the present invention comprises a compound selected from the above-described ones as an active ingredient, a novel preventive agent or remedy for allergy according to the present invention comprises a compound selected from the above-described ones as an active ingredient, and a novel preventive agent or remedy for urinary incontinence according to the present invention comprises a compound selected from the above-described ones as an active ingredient.

Use for the preparation of a medicament according to the present invention comprises using a compound selected from the above-described ones, use for the preparation of a preventive agent or remedy for tachykinin-mediated diseases according to the present invention comprises using a compound selected from the above-described ones, use for the preparation of an inhibitor of an $NK_1$ receptor and/or an $NK_2$ receptor according to the present invention comprises using a compound selected from the above-described ones, use for the preparation of a preventive agent or remedy for asthma and/or bronchitis according to the present invention comprises using a compound selected from the above-described ones, use for the preparation of a preventive agent or remedy for rhinitis according to the present invention comprises using a compound selected from the above-described ones, use for the preparation of a preventive agent or remedy for allergy according to the present invention comprises using a compound selected from the above-described ones, and use for the preparation of a preventive agent or remedy for urinary incontinence according to the present invention comprises using a compound selected from the above-described ones.

In the salts of an optically active sulfoxide derivative according to the present invention, 1-{2-[(2R)-(3,4-dichlorophenyl)-4-(3,4,5-trimethoxybenzoyl)morpholin-2-yl]ethyl}spiro[benzo(c)thiophene-1(3H),4'-piperidin]-(2S) oxide is a compound represented by the following structural formula (I):

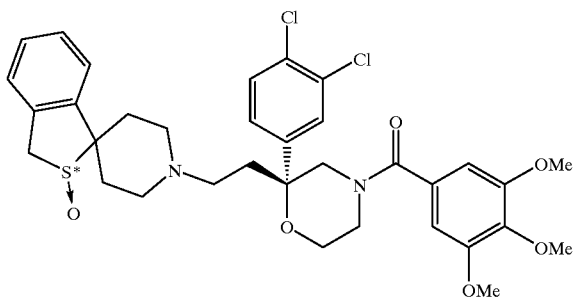

(wherein, >S*→O represents a sulfoxide group wherein the oxygen atom is attached to the sulfur atom in the S absolute configuration).

Of the hydrochloride and fumarate of 1-{2-[(2R)-(3,4-dicholorophenyl)-4-(3,4, 5-trimethoxybenzoyl)morpholin-2-yl]ethyl}spiro[benzo(c)thiophene-1(3H),4'-piperidin]-(2S)-oxide according to the present invention, the hydrochloride is the more preferred.

"The hydrochloride and fumarate of 1-{2-[(2R)-(3,4-dichlorophenyl)4-(3,4,5-trimethoxybenzoyl)morpholin-2-yl]ethyl}spiro[benzo(c)thiophene-1(3H),4 '-piperidin]-(2S)-oxide" according to the present invention happen to be solvates, absorbing water or a recrystallization solvent when they are allowed to stand in the air or are recrystallized. Such salts are also embraced in the present invention.

The salts of an optically active sulfoxide derivative according to the present invention can be prepared by converting "1-{2-[(2R)-(3,4-dichlorophenyl)-4-(3,4,5-trimethoxybenzoyl)morpholin-2-yl]ethyl}spiro[benzo(c) thiophene-1(3H),4'-piperidin]-(2S)-oxide" obtained in accordance with Referential Examples, described below, into its hydrochloride or fumarate in a known manner.

The novel salts of an optically active sulfoxide derivative according to the present invention exhibit excellent antagonistic action against both substance P receptors and neurokinin A receptors and besides, they have low toxicity so that they are useful as a preventive agent or remedy for tachykinin-mediated diseases. Examples of such diseases are diseases of the central nervous system such as anxiety, depression, psychosis and schizophrenia; neurodegenerative diseases such as dementia of AIDS, Alzheimer's senile dementia, Alzheimer's disease, Down's syndrome, demyelinating disease, amyotrophic lateral sclerosis, neuropathy, peripheral neuropathy and neuralgia; respiratory diseases such as chronic obstructive pulmonary disease, bronchitis, pneumonia, bronchoconstriction, asthma and cough; inflammatory diseases such as inflammatory bowel disease (IBD), psoriasis, fibrosis, arthrosteitis, degenerative arthritis and rheumatoid arthritis; eczema; allergies such as rhinitis; hypersensitivity diseases such as hypersensitivity to vines; ophthalmological diseases such as conjunctivitis, vernal conjunctivitis, vernal catarrh, destruction of the blood-aqueous humor barrier caused by various inflammatory eye diseases, elevated introcular pressure and miosis; skin diseases such as contact dermatitis, atopic dermatitis, urticaria and other eczematoid dermatitis; addictions such as alcohol dependency; somatic diseases caused by stress; sympathetic reflex dystrophy such as hand and shoulder syndrome; dysthymia; undesirable immune reactions such as rejection of grafts; diseases relating to immunopotentiation such as systemic lupus erythematosus or immunosuppression; digestive diseases such as diseases caused by abnormalities in nerves regulating the organs, colitis, ulcerative colitis and Crohn's disease; emesis such as emesis induced by adverse effects of X-ray irradiation and chemotherapy, poisons, toxins, pregnancy, vestibular disorders, postoperative illness, gastrointestinal occlusion, reduced gastrointestinal movement, visceral pain, migraine headache, increased intracranial pressure, reduced intracranial pressure or adverse reaction induced by administration of various medicaments; urinary bladder functional diseases such as cystitis and urinary incontinence; eosinophilia caused by collagen diseases, scleriasis or Fasciola hepatica infection; diseases caused by abnormal blood flow due to vasodilation or vasoconstriction such as angina pectoris, migraine headache and Reynauds's disease; and pain of pain nociceptive reception such as migraine headache, headache and toothache.

Examples of the administration route of the salts of an optically-active sulfoxide derivative according to the present invention include oral administration by, for example, tablets, capsules, granules, powders or syrups, and parenteral administration by injection, suppository or the like. Such pharmaceutical preparations can be prepared by methods well known in the art by using additives such as excipients (examples include organic excipients such as sugar derivatives, e.g., lactose, sucrose, dextrose, mannitol and sorbitol; starch derivatives, e.g., corn starch, potato starch, a-starch, dextrin and carboxymethyl starch; cellulose derivatives, e.g., crystalline cellulose, low-substituted hydroxypropylcellulose, hydroxypropylmethylcellulose, carboxymethylcellulose, carboxymethylcellulose calcium and internally cross-linked carboxymethylcellulose sodium; gum arabic; dextran; and pullulan; and inorganic excipients such as silicate derivatives, e.g., light anhydrous silicic acid, synthetic aluminum silicate and magnesium aluminate metasilicate; phosphates, e.g., calcium phosphate; carbonates, e.g., calcium carbonate; and sulfates, e.g., calcium sulfate), lubricants (examples include stearic acid; metal salts of stearic acid such as calcium stearate and magnesium stearate; talc; colloidal silica; waxes such as bee gum and spermaceti; boric acid; adipic acid; sulfates such as sodium sulfate; glycol; fumaric acid; sodium benzoate; DL leucine; sodium salts of aliphatic acids; laurylsulfates such as sodium laurylsulfate and magnesium laurylsulfate; silicic acids such as anhydrous silicic acid and silicate hydrate; and the above-described starch derivatives), binders (examples include polyvinyl pyrrolidone, macrogol and compounds similar to the above-exemplified excipients), disintegrators (examples include compounds similar to the above-exemplified excipients and chemically modified starches and celluloses such as crosscarmellose sodium, carboxymethyl starch sodium and crosslinked polyvinylpyrrolidone), stabilizers (examples include paraoxybenzoates such as methylparaben and propylparaben; alcohols such as chlorobutanol, benzyl alcohol and phenylethyl alcohol; benzalkonium chloride; phenol and phenol derivatives such as cresol; thimerosal; dehydroacetic acid; and sorbic acid), corrigents (examples include ordinarily-employed sweetening agents, sour agents and perfumes) and/or diluents.

The dose of the compound of the invention will vary depending on the condition and age of the patient, administration route, and the like. The compound is orally administered in an amount of from 0.01 mg/kg weight (preferably 0.1 mg/kg weight, lower limit) to 100 mg/kg weight (preferably 50 mg/kg weight, upper limit) in a single dose; on the other hand, the compound is intravenously administered in an amount of 0.01 mg/kg weight (preferably 0.05 mg/kg weight, lower limit) to 100 mg/kg weight (preferably 50 mg/kg weight, upper limit) in a single dose. It is desired to administer the compound from once to several times a day depending on the condition of the patient, i.e., human or other mammal.

THE EXAMPLES

The present invention will hereinafter be described in further detail by examples, referential examples, tests and formulation examples.

Example 1

1-{2-[(2R)-(3,4-Dichlorophenyl)-4-(3,4,5-trimethoxybenzoyl)morpholin-2-yl]ethyl}spiro[benzo(c)thiophene-1(3H),4'-piperidin]-(2S)-oxide hydrochloride In 220 ml of 2-propanol, 21.4 g (31.8 mmol) of 1-{2-[(2R)-(3,4-dichlorophenyl)-4-(3,4,5-trimethoxybenzoyl)morpholin-2-yl]ethyl}spiro[benzo(c)thiophene-1(3H),4'-piperidin]-(2S)-oxide were dissolved. To the resulting solution, 39.8 ml (159 mmol) of a 4N solution of hydrogen chloride in dioxane were added dropwise at 0° C. over 20 minutes, followed by stirring for 30 minutes. The reaction mixture was concentrated to dryness by distilling off the solvent under reduced pressure. To the residue, 220 ml of diethyl ether were added, followed by distillation under reduced pressure. After this procedure was repeated twice, 110 ml of diethyl ether were added to the residue to afford crystals. The crystals were collected by filtration and washed with diethyl ether, whereby 20.99 g of the title compound were obtained.

$[\alpha]^{25}{}_D$:+38.0(c=0.58, methanol); Melting point: 162° C. to 166° C.; Nuclear magnetic resonance spectrum (400 MHz, CDCl$_3$)δ ppm: 13.2 (1H, br), 7.25–7.70 (7H, m), 6.74 (2H, s), 2.93–4.60 (14H, m), 4.49 (1H, d, J=16 Hz), 4.10 (1H, d, J=16 Hz), 3.87 and 3.94 (total 9H, s each), 2.63 (1H, d, J=15 Hz), 2.47 (1H, m), 2.20 (1H, m), 1.91 (1H, d, J=15 Hz). Infrared absorption spectrum: $v_{max}$ cm$^{-1}$ (KBr): 3429, 2963, 2937, 2482, 2404, 1635, 1584; Mass spectrum (FAB) m/z: 673 (free form, (M+H)$^+$); Elementary analysis (for $C_{34}H_{39}N_2O_6SCl_3 \cdot 0.6H_2O$ (%)); Calculated: C: 56.65, H: 5.62, N: 3.89, S: 4.45, Cl: 14.75; Found: C: 56.40, H: 5.91, N: 3.75, S: 4.16, Cl: 14.82; Analysis by high-performance liquid chromatography: Column: TSKgel ODS-80Ts (250× 4.6 mmφ); (product of TOSOH CORPORATION); Solvent: a 45:55 mixture of 0.1% ammonium acetate acetonitrile solution and a 0.1% aqueous ammonium acetate solution; Flow rate: 1.0 ml/min; Retention time: 21.0 min.

Example 2

1-{2-[(2R)-(3,4-Dichlorophenyl)-4-(3,4,5-trimethoxybenzoyl)morpholin-2-yl]ethyl}spiro[benzo(c)thiophene-1(3H),4'-piperidin]-(2S)-oxide fumarate In 230 ml of ethyl acetate, 400 mg (3.45 mmol) of fumaric acid were dissolved, followed by the addition of 2.32 g (3.44 mmol) of 1-{2-[(2R)-(3,4-dichlorophenyl)-4-(3,4,5-trimethoxybenzoyl)morpholin- 2-yl]ethyl}spiro[benzo(c)thiophene-1(3H),4'-piperidin]-(2S)-oxide to the resulting solution to dissolve the latter in the former. The solution was allowed to stand overnight. The solvent of the reaction mixture was distilled off under reduced pressure to give a residue. The residue was dissolved in 5 ml of methanol, and then 200 ml of diisopropyl ether were added to the solution to afford crystals. The crystals were collected by filtration, whereby 2.52 g of the title compound were obtained.

$[\alpha]^{25}_D$:+24.9 (c=1.00, methanol); Melting point: 151° C. to 155° C.; Nuclear magnetic resonance spectrum (400 MHz, CDCl$_3$) δ ppm: 7.2–7.7 (7H, m), 6.62 (2H, s), 6.57 and 6.55 (total 2H, s each), 4.54 (1H, d, J=17 Hz), 3.94 (1H, d, J=17 Hz), 1.8–4.5 (18H, m), 3.77 and 3.69 (total 9H, s each); Infrared absorption spectrum: $v_{max}$ cm$^{-1}$ (KBr): 3422, 2839, 1711, 1637, 1584, 1465, 1239, 1127; Mass spectrum (FAB) m/z: 673 (free form, (M+H)$^+$); Elementary analysis (for C$_{38}$H$_{42}$N$_2$O$_{10}$SCl$_2$·H$_2$O (%)); Calculated: C: 56.50, H: 5.49, N: 3.47, S: 3.97, Cl: 8.78; Found: C: 56.77, H: 5.39, N: 3.34, S: 3.55, Cl: 8.33.

Referential Example 1

Spiro[benzo[c]thiophene-1(3H),4'-piperidin]-(2S)-oxide hydrochloride

[Referential Example 1(a)]

1'-tert-Butoxycarbonyl-spiro[benzo[c]thiophene-1(3H),4'-piperidine]

In 800 ml of tetrahydrofuran, 81.0 g (0.40 mole) of 2-bromobenzylthiol were dissolved, followed by the dropwise addition of 516 ml (0.84 mole) of n-butyl lithium (1.6 mole, a hexane solution) at −78° C. over 6 hours. After stirring at the same temperature for 1.5 hours, a solution of 79.5 g (0.40 mole) of N-tert-butoxycarbonyl-4-piperidone in 800 ml of tetrahydrofuran was added dropwise to the reaction mixture over 3 hours and then the mixture was stirred for a further 1 hour. A saturated aqueous solution of ammonium chloride was added to the reaction mixture and the mixture was extracted with ethyl acetate. The organic layer was washed with a saturated aqueous solution of sodium chloride and dried over anhydrous sodium sulfate, and the solvent was distilled off under reduced pressure to afford a residue. To the residue, 2 liters of 4N sulfuric acid were added and the mixture was heated under reflux for 14 hours. Under ice-cooling, the reaction mixture was made alkaline with 350 g (8.75 mole) of sodium hydroxide, followed by addition of 102 g (0.47 mole) of di-tert-butyl dicarbonate. The resulting mixture was stirred for 1 hour. The reaction mixture was extracted with methylene chloride. The organic layer was washed with a saturated aqueous solution of sodium chloride and then dried over anhydrous sodium sulfate. The residue obtained by distilling off the solvent of the extract under reduced pressure was purified by chromatography on a silica gel column (eluting solvent; n-hexane:ethyl acetate=97:3), whereby 56 g of the title compound were obtained as white crystals.

Melting point: 131.0 to 132.5° C. (n-hexane—ethyl acetate); Nuclear magnetic resonance spectrum (400 MHz, CDCl$_3$) δ ppm: 7.28–7.24 (31H, m), 7.17–7.15 (1H, m), 4.23 (2H, br, s), 4.19 (2H, s), 3.02 (2H, br, s), 2.07 (2H, dt, J=4.4, 13 Hz), 1.88 (2H, m), 1.49 (9H, s); Infrared absorption spectrum: $v_{max}$ cm$^{-1}$ (KBr): 2970, 1680, 1428, 1234, 1163; Mass spectrum (FAB) m/z: 306 ((M+H)$^+$).

[Referential Example 1(b)]

1'-tert-Butoxycarbonyl-spiro[benzo[c]thiophene-1(3H),4'-piperidin]-2-oxide

In 420 ml of chloroform, 42.0 g (0.14 mole) of the 1'-tert-butoxycarbonyl-spiro[benzo[c]thiophene-1(3H),4'-piperidine] obtained in Referential Example 1(a) were dissolved, followed by the addition of 12.7 g (0.15 mole) of sodium bicarbonate. To the resulting mixture, 28.0 g (85% content, 0.14 mole) of m-chloroperbenzoic acid were added in small portions under ice-cooling. After stirring of the mixture for 30 minutes under ice-cooling, 10 g of potassium iodide were added thereto and the mixture was stirred at room temperature for 30 minutes. The reaction mixture was washed with water and a saturated aqueous solution of sodium chloride and dried over anhydrous sodium sulfate, and the solvent was removed by distillation under reduced pressure to obtain a residue. The residue was purified by chromatography on a silica gel column (eluting solvent; n-hexane: ethyl acetate=1:1), whereby 42 g of the title compound were obtained as white crystals.

Melting point: 103° C. to 107° C. (diisopropyl ether); Nuclear magnetic resonance spectrum (400 MHz, CDCl$_3$) δ ppm: 7.37–7.32 (3H, m), 7.25–7.23 (1H, m), 4.37 (1H, d, J=16.7 Hz), 4.13 (2H, br, s), 4.05 (2H, d, J=16.7 Hz), 3.21 (2H, br, s), 2.43 (1H, m), 2.21 (1H, m), 1.70 (1H, m), 1.61 (1H, m), 1.50 (9H, s); Infrared absorption spectrum: $v_{max}$ cm$^{-1}$ (KBr): 2985, 1686, 1429, 1368, 1286, 1167; Mass spectrum (FAB) m/z: 322 ((M+H)$^+$).

[Referential Example 1(c)]

Spiro[benzo[c]thiophene-1(3H),4'-piperidin]-2-oxide

In 420 ml of 2-propanol, 42.0 g (0.13 mole) of the 1'-tert-butoxycarbonyl-spiro[benzo[c]thiophene-1(3H),4'-piperidin]-2-oxide obtained in Referential Example 1(b) were dissolved, followed by addition of 150 ml of a 4N solution of hydrogen chloride in dioxan under ice-cooling, and the mixture was stirred for 4 hours. To the reaction mixture, 200 ml of diethyl ether were added. After, the mixture was allowed to stand for 1 hour under ice-cooling, to afford crystals. The crystals were collected by filtration. The resulting crystals were dissolved in 200 ml of a 5% aqueous solution of sodium hydroxide. The solution was extracted with methylene chloride. The organic layer was dried over anhydrous sodium sulfate and the solvent was distilled off under reduced pressure, whereby 21.7 g of the title compound was obtained as a white amorphous product.

[Referential Example 1(d)]

Spiro[benzo[c]thiophene-1(3H),4'-piperidin]-(2S)-oxide(S)-(+)-mandelate

In 3350 ml of acetonitrile, 33.51 g (0.15 mole) of the spiro[benzo[c]thiophene-1-(3H),4'-piperidin]-2-oxide obtained in Referential Example 1(c) were dissolved with heating, and then 11.52 g (75.7 mmol) of (S)-(+)-mandelic acid were added thereto. The resulting solution was allowed to stand at room temperature overnight. Crystals precipitated in the reaction mixture were collected by filtration, whereby 19.62 g of the title compound were obtained as white crystals. The filtrate was concentrated under reduced pressure to afford a residue. The residue was dissolved in a 5% aqueous solution of sodium hydroxide, followed by extraction with methylene chloride. The organic layer was dried over anhydrous sodium sulfate and then the solvent was distilled off under reduced pressure to afford 22.01 g (99.5 mmol) of a residue. The residue was dissolved in 2200 ml of acetonitrile with heating and in the resulting solution, 7.22 g (47.5 mmol) of (R)-(−)mandelic acid were dissolved. The resulting solution was allowed to stand overnight at room temperature to afford crystals. The crystals were collected by filtration, whereby 15.91 g of spiro[benzo[c]thiophene-1 (3H),4'-piperidin]-(2R)-oxide (R)-(−)-mandelate were obtained as white crystals. The filtrate was further concentrated under reduced pressure and the residue was dissolved in a 5% aqueous solution of sodium hydroxide. The resulting solution was extracted with methylene chloride. The organic layer was dried over anhydrous sodium sulfate and the solvent was distilled off under reduced pressure to afford 11.51 g (52.0 mmol) of a residue. The residue was dissolved in 1100 ml of acetonitrile with heating, and then 3.95 g (26.0 mmol) of (S)-(+)-mandelic acid were added thereto to be dissolved. The resulting solution was allowed to stand overnight at room temperature to afford crystals. The crystals were collected by filtration to give 4.73 g of the title compound as white crystals. The batches of title compound thus obtained were combined, 24.00 g of it were dissolved in 9.6 liters of acetonitrile with heating, and the solution was allowed to stand overnight at room temperature to afford 20.13 g of crystals. The optical purity of the crystals was determined to be 99.8% ee as a result of analysis by HPLC of 1'-tert-butoxycarbonyl-spiro[benzo[c]thiophene-1(3H), 4'-piperidin]-(2S)-oxide which was prepared from the crystals.

Melting point: 197 to 200° C.; $[\alpha]_D^{24}$:+78.3 (c=1, methanol); Infrared absorption spectrum $\nu_{max}$ cm$^{-1}$ (KBr): 3388, 3029, 1629, 1332, 1017; Mass spectrum (EI) m/z: 221 (free form M$^+$).

[Referential Example 1(e)]

1'-tert-Butoxycarbonyl-spiro[benzo[c]thiophene-1 (3H),4'-piperidin]-(2S)-oxide

In 200 ml of a 5% aqueous solution of sodium hydroxide, 19.88 g (53.2 mmol) of the (S)-(+)mandelate salt synthesized in Referential Example 1(d) were dissolved, followed by extraction with methylene chloride (200 ml, three times). The organic layer was dried over anhydrous magnesium sulfate and then the solvent was distilled off under reduced pressure to afford a residue. In 300 ml of methylene chloride, 11.80 g of the residue were dissolved, followed by successive addition of 11.2 ml (79.8 mmol) of triethylamine and 17.4 g (79.8 mmol) of di-tert-butyl dicarbonate under ice-cooling After stirring at room temperature overnight, the reaction mixture was diluted with 200 ml of methylene chloride, washed with a 10% aqueous solution of citric acid and a saturated aqueous solution of sodium bicarbonate and then dried over anhydrous magnesium sulfate. The solvent was distilled off under reduced pressure to afford a residue. The residue was purified by chromatography on a silica gel column (eluting solvent: n-hexane:ethyl acetate=4:6 to 3:7), followed by recrystallization from diisopropyl ether, whereby 13.1 g of the title compound were obtained as white crystals.

Melting point: 129.0 to 130.5° C. (diisopropyl ether); $[\alpha]_D^{24}$:+57.1 (c=1, methanol); HPLC analysis; Column: Chiral Cel OD (250×4.6 mmϕ); Eluting solvent: n-hexane: 2-propanol=80:20; Flow rate: 0.8 ml/min; Retention time: 18.1 min.

The nuclear magnetic resonance spectrum, infrared absorption spectrum and mass spectrum of the crystals were identical to those of the racemic form prepared in Referential Example 1(b).

[Referential Example 1(f)]

Spiro[benzo[c]thiophene-1(3H),4'-piperidin]-(2S)-oxide hydrochloride

In 130 ml of 2-propanol, 13.0 g (40.4 mmol) of the 1'-tert-butoxycarbonyl-spiro[benzo[c]thiophene-1(3H),4'-piperidin]-(2S)-oxide obtained in Referential Example 1(e) were dissolved, followed by the addition of 50 ml of 4N solution of hydrogen chloride in dioxane under ice-cooling. After stirring for one hour under ice-cooling, the reaction mixture was stirred for a further 6 hours at room temperature. The reaction mixture was concentrated under reduced pressure to give a residue. To the residue, 200 ml of diethyl ether were added and the solvent was distilled off from the resulting mixture under reduced pressure (three times). The residue was recrystallized from 300 ml of a 1:2 mixture of methanol and diethyl ether, whereby 9.10 g of the title compound were obtained as white crystals.

Melting point: 209.5 to 210.5° C.; $[\alpha]_D^{24}$:+63.8 (c=1, methanol);

Referential Example 2

1'-tert-Butoxycarbonyl-spiro[benzo[c]thiophene-1 (3H),4 '-piperidin]-(2S)-oxide

In 5 ml of methylene chloride, 250 mg (0.82 mmol) of the 1'-tert-butoxycarbonyl-spiro[benzo[c]thiophene-1(3H),4'-piperidine] obtained in Referential Example 1(a) were dissolved. To the resulting solution, 308 mg (0.82 mmol) of (3'S,2R)-(−)-N-(phenylsulfonyl)(3,3-dichlorocamphoryl) oxazolidine prepared in accordance with the method of F. A. Davis et al. (J. Am. Chem. Soc., 114, 1428(1992)) were added and the resulting mixture was stirred at room temperature overnight. To the reaction mixture, 500 mg of potassium iodide were added, followed by stirring at room temperature for 30 minutes. The reaction mixture was washed successively with water and a saturated aqueous solution of sodium chloride and dried over anhydrous sodium sulfate, and then the solvent was distilled off under reduced pressure. The residue was purified by chromatography on a silica gel column (n-hexane: ethyl acetate=1:2), whereby 245 mg of the title compound were obtained.

Optical purity: 94% ee

Referential Example 3

3-(3,4-Dichlorophenyl)-3-buten-1-ol tert-butyldimethylsilyl ether

[Referential Example 3(a)]

Methyl 3-(3,4-dichlorophenyl)-3-butenoate

To 300 ml of diethyl ether, 11.31 g (0.47 mole) of a piece of metallic magnesium were added, followed by the addition of a small amount of iodine thereto. After the mixture was allowed to stand for 1 hour, a solution of 102.87 g (0.46 mole) of 1-bromo-3,4-dichlorobenzene in diethyl ether (150 ml) was slowly added dropwise thereto. To the reaction mixture, 150 ml of diethyl ether were added and then 60.33 g (44.3 mmol) of anhydrous zinc chloride were slowly added and the resulting mixture was stirred for 1 hour. After 3.10 g (4.42 mmol) of bis(triphenylphosphine)palladium chloride were added to the reaction mixture, a solution of 34.15 ml (42.8 mmol) of diketene in diethyl ether (600 ml) was added dropwise to the resulting mixture. The reaction mixture was stirred at room temperature for 30 minutes.

The reaction mixture was poured into 1 liter of 1N hydrochloric acid which had been cooled with ice-water, and the mixture was extracted with diethyl ether (500 ml, three times). The organic layers were combined, followed by extraction with a 1N aqueous solution of sodium hydroxide (700 ml, three times). The water layers were combined and then made acidic with concentrated hydrochloric acid under ice-cooling. The resulting solution was extracted with diethyl ether (500 ml, three times) and the organic layers were dried over anhydrous magnesium sulfate and the solvent was distilled off under reduced pressure to afford a residue, which was dissolved in 350 ml of methanol. To the solution, 10 ml of concentrated sulfuric acid were added, followed by heating under reflux for 30 minutes. After cooling the reaction mixture to room temperature, the reaction mixture was neutralized with a saturated aqueous solution of sodium bicarbonate and the methanol was distilled off under reduced pressure to afford a residue, which was extracted with methylene chloride (200 ml, three times). The organic layers were combined, dried over anhydrous magnesium sulfate and then concentrated under reduced pressure to afford a residue. The residue was distilled under reduced pressure, whereby 69.13 g (62%) of the title compound were obtained as a pale yellow oil.

Boiling point: 144 to 146° C. (5 mm Hg)

Nuclear magnetic resonance spectrum (400 MHz, $CDCl_3$) δ ppm: 7.51 (1H, d, J=2.2 Hz), 7.40 (1H, d, J=8.2 Hz), 7.25 (1H, dd, J=8.2, 2.2 Hz), 5.55 (1H, s), 5.30 (1H, s), 3.67 (3H, s), 3.49 (2H, s).

[Referential Example 3(b)]

3-(3,4-Dichlorophenyl)-3-buten-1-ol tert-butyldimethylsilyl ether

In 500 ml of anhydrous tetrahydrofuran, 11.76 g (0.28 mole) of lithium aluminum hydride were suspended. To the suspension, a solution of 69.06 g (0.28 mole) of the methyl 3-(3,4-dichlorophenyl)-3-butenoate prepared in Referential Example 3(a) in anhydrous tetrahydrofuran (500 ml) was added dropwise at 0° C. over 15 minutes under an atmosphere of nitrogen. After stirring at the same temperature for 30 minutes, 500 ml of water and 500 ml of a 10% aqueous solution of sodium hydroxide were gradually added to the reaction mixture. The resulting mixture was stirred for a further 1 hour at room temperature.

The reaction mixture was filtered through Celite. The filtrate was extracted with ethyl acetate (500 ml, three times). The organic layers were combined and dried over anhydrous magnesium sulfate and then concentrated under reduced pressure to afford a residue. The residue was dissolved in 250 ml of anhydrous dimethylformamide. To the resulting solution, 47.12 ml (0.34 mole) of triethylamine, 6.88 g (0.06 mole) of 4-dimethylaminopyridine and 50.96 g (0.34 mole) of tert-butyldimethylsilyl chloride were successively added under ice-cooling and the mixture was stirred for 2 hours under ice-cooling.

To the reaction mixture, 1 liter of ethyl acetate was added. The resulting mixture was washed successively with 10% hydrochloric acid, which had been ice-cooled, and a saturated aqueous solution of sodium chloride and then dried over anhydrous magnesium sulfate. The residue obtained by distilling off the solvent of the mixture under reduced pressure was purified by flash chromatography on a silica gel column (eluting solvent: n-hexane: ethyl acetate=50:1 to 20:1), whereby 43.52 g (47%) of the title compound were obtained as a colorless oil.

Nuclear magnetic resonance spectrum (400 MHz, $CDCl_3$) δ ppm: 7.50 (1H, d, J=2.1 Hz), 7.38 (1H, d, J=8.1 Hz), 7.24 (1H, dd, J=8.1, 2.1 Hz), 5.35 (1H,s), 5.16 (1H,s), 3.70 (2H, t, J=6.9 Hz), 2.67 (2H, t, J=6.9 Hz), 0.89 (9H, s), 0.00 (6H, s).

Referential Example 4

3-(3,4-Dichlorophenyl)-3-buten-1-ol tert-butyldimethylsilyl ether

[Referential Example 4(a)]

3-(3,4-Dichlorophenyl)-3-oxo-1-propanol

In 2.4 liters of ethanol, 119 g (0.46 mole) of ethyl 3-(3,4-dichlorophenyl)-3-oxopropionate were dissolved. To the resulting solution, 115 ml (0.68 mole) of ethyl orthoformate and 4.4 g (2.28 mmol) of p-toluenesulfonic acid were added, followed by heating under reflux for 8 hours. The reaction mixture was poured into 1 liter of a saturated aqueous solution of sodium bicarbonate and the mixture was extracted with ethyl acetate (700 ml, three times). The organic layers were combined, washed with a saturated aqueous solution of sodium chloride and then dried over anhydrous sodium sulfate. After the solvent was distilled off under reduced pressure, the residue was dissolved in 800 ml of tetrahydrofuran. The resulting solution was added dropwise to a suspension of 25.9 g (0.68 mole) of lithium aluminum hydride in 4 liters of tetrahydrofuran over 1 hour under ice-cooling. After stirring at 0° C. for 2 hours, 250 ml of water and 125 ml of a 10% aqueous solution of sodium hydroxide were added and the mixture was stirred at room temperature for a further 1 hour. The reaction mixture was filtered through Celite. The filtrate was poured into 1 liter of a saturated aqueous solution of sodium chloride, followed by extraction with ethyl acetate. The organic layer was dried over anhydrous sodium sulfate and concentrated under reduced pressure. A residue was dissolved in 500 ml of chloroform. Under ice-cooling, 500 ml of 50% trifluoroacetic acid were added dropwise to the resulting solution over 30 minutes and the mixture was stirred for 30 minutes. The reaction mixture was diluted with 300 ml of methylene chloride. The organic layer was washed with water and a saturated aqueous solution of sodium bicarbonate and dried over anhydrous sodium sulfate, and then the solvent was distilled off under reduced pressure. The residue was purified by chromatography on a silica gel column (eluting solvent: n-hexane: ethyl acetate=9:1), whereby 46 g of the title compound were obtained as white crystals.

Nuclear magnetic resonance spectrum (270 MHz, $CDCl_3$) δ ppm: 8.05 (1H, d, J=2.0 Hz), 7.79 (1H, dd, J=2.0, 8.1 Hz), 7.57 (1H, d, J=8.1 Hz), 4.04 (2H, m), 3.19 (2H, t, J=5.3 Hz), 2.44 (1H, t, J=6.6 Hz, $D_2O$ disappeared).

[Referential Example 4(b)]

3-(3,4-Dichlorophenyl)-3-oxo-1-propanol tert-butyldimethylsilyl ether

In 460 ml of dimethylformamide, 46.0 g (0.21 mole) of the 3-(3,4-dichlorophenyl)-3-oxo-1-propanol obtained in Referential Example 4(a) were dissolved, followed by the addition of 35 ml (0.25 mole) of triethylamine and 38.0 g (0.25 mole) of tert-butyldimethylchlorosilane under ice-cooling. The resulting mixture was stirred at 0° C. for 2 hours. The reaction mixture was poured into water and the mixture was extracted with ethyl acetate. The organic layer was washed with a saturated aqueous solution of sodium chloride and dried over anhydrous sodium sulfate, and the solvent was distilled off under reduced pressure to give a residue, which was purified by chromatography on a silica gel column (eluting solvent: n-hexane: ethyl acetate=96:4), whereby 66.1 g of the title compound were obtained as white crystals.

Nuclear magnetic resonance spectrum (270 MHz, CDCl$_3$) δ ppm: 8.06 (1H, d, J=2.0 Hz), 7.80 (1H, dd, J=2.0, 8.3 Hz), 7.55 (1H, d, J=8.3 Hz), 4.04 (2H, t, J=6.3 Hz), 3.13 (2H, t, J=6.3 Hz), 0.85 (9H, s), 0.04 (6H, s).

[Referential Example 4(c)]

3-(3,4-Dichlorophenyl)-3-buten-1-ol tert-butyldimethylsilyl ether

To 2 liters of dried benzene, 215 g (0.60 mole) of methyltriphenylphosphonium bromide and 54 g (0.48 mole) of potassium t-butoxide were added and the mixture was stirred at room temperature for 9 hours. In 800 ml of benzene, 40 g (0.12 mole) of the 3-(3,4-dichlorophenyl)-3-oxo-1-propanol tert-butyldimethylsilyl ether obtained in Referential Example 4(b) were dissolved and the resulting solution was added dropwise to the reaction mixture over 2.5 hours. To the reaction mixture, 1 liter of water was added, followed by stirring under ice-cooling for 30 minutes. The organic layer was washed with water and a saturated aqueous solution of sodium chloride and dried over anhydrous sodium sulfate, and the solvent was distilled off under reduced pressure to give a residue, which was purified by chromatography on a silica gel column (eluting solvent: n-hexane), whereby 23.5 g of the title compound were obtained. Various spectral data were identical to those obtained in Referential Example 3(b).

Referential Example 5

3-(3,4-Dichlorophenyl)-3-buten-1-ol tert-butyldimethylsilyl ether

To 2 ml of diethyl ether, 129 mg (5.31 mmol) of a piece of metallic magnesium were added, followed by addition of a small amount of iodine. To the resulting mixture, a solution of 1.01 g (4.47 mmol) of 3,4-dichlorobromobenzene in diethyl ether (1 ml) was added dropwise and the mixture was stirred at room temperature for 1 hour under an atmosphere of nitrogen to afford Grignard reagent. In 5 ml of dried tetrahydrofuran, 500 mg (1.60 mmol) of 3-iodo-3-buten-1-ol tert-butyldimethylsilyl ether and 34 mg (0.048 mmol) of bistriphenylphosphine palladium(II) chloride were dissolved, followed by dropwise addition of the Grignard reagent at room temperature under an atmosphere of nitrogen. While heating, the solvent of the reaction mixture was distilled off to afford a residue. The residue was stirred at 60° C. for 1 hour and then was poured into an aqueous solution of ammonium chloride and the mixture was extracted with ethyl acetate. The organic layer was washed with a saturated aqueous solution of sodium chloride and dried over anhydrous sodium sulfate, and the solvent was distilled off under reduced pressure. The residue was purified by column chromatography over silica gel (eluting solvent: n-hexane), whereby 422 mg of the title compound were obtained. The spectral data of this product were identical to those of the compound obtained in Referential Example 3(b).

Referential Example 6

1-{2-[(2R)-(3,4-Dichlorolphenyl)-4-(3,4,5-trimethoxybenzoyl)morpholin-2-yl]ethyl}spiro[benzo[c]thiophene-1(3H),4'-piperidin]-(2S)-oxide

[Referential Example 6(a)]

4-tert-Butyldimethylsilyloxy-(2R)-(3,4-dichlorophenylhbutan-1,2-diol

In a mixture of 500 ml of 2-methyl-2-propanol and 500 ml of water, 790 mg (1.01 mmol) of (DHQD)$_2$-PHAL (hydroquinidine 1,4-phthalazindiyl diether), 100.19 g (0.30 mole) of K$_3$Fe(CN)$_6$ (potassium ferricyanide), 42.06 g (0.30 mole) of potassium carbonate and 0.516 ml (0.20 mmol) of osmium tetraoxide (a 0.393M solution in toluene) were dissolved, followed by the addition of 33.61 g (0.10 mole) of 3-(3,4-dichlorophenyl)-3-buten-1-ol tert-butyldimethylsilyl ether at 0° C. The resulting mixture was stirred for 5 hours at 0° C. To the reaction mixture, 150 g of sodium sulfite were added and the mixture was stirred at room temperature for 1 hour. The reaction mixture was extracted with ethyl acetate (800 ml, thrice). The organic layers were combined and dried over anhydrous magnesium sulfate. After the solvent was distilled off under reduced pressure, the residue was purified by flash column chromatography over silica gel (eluting solvent: n-hexane: ethyl acetate=5:1 to 1:1), whereby 32.3 g (87%) of the title compound were obtained as a colorless oil.

Optical purity: 97% ee; $[\alpha]_D^{24}$:+11.39 (c=1.01, methanol); Nuclear magnetic resonance spectrum (400 MHz, CDCl$_3$) δ ppm: 7.57 (1H, d, J=2.1 Hz), 7.43 (1H, d, J=8.1 Hz), 7.24 (1H, dd, J=8.1, 2.1 Hz), 5.00 (1H, s), 3.80 (1H, ddd, J=10.4, 3.8, 3.8 Hz), 3.5–3.7 (3H, m), 2.51 (1H, dd, J=8.0,5.2 Hz), 2.37 (1H, ddd, J=15.0, 11.1, 4.0 Hz), 1.86 (1H, ddd, J=15.0, 2.9, 2.9 Hz), 0.89 (9H, s), 0.04 (3H, s), −0.01 (3H, s).

[Referential Example 6(b)]

4(tert-Butyldimethylsilyloxy)-(2R)-(3,4-dichlorophenyl)-1-[N-(tert-butoxycarbonyl)-N-(2-hydroxyethyl)amino]-2-butanol In 80 ml of pyridine, 39.9 g (109 mmol) of the 4-tert-butyldimethylsilyloxy-(2R)-(3,4-dichlorophenyl)butan-1,2-diol obtained in Referential Example 6(a) were dissolved, followed by the addition of 31.3 g (164 mmol) of p-toluenesulfonyl chloride. The mixture was stirred at room temperature for 2 days under an atmosphere of nitrogen. The reaction mixture was diluted with water and extracted with ethyl acetate. The organic layer was washed with water and a saturated aqueous solution of sodium chloride and dried over anhydrous sodium sulfate, and the solvent was distilled off under reduced pressure to give a residue, which was dissolved in 600 ml of acetonitrile. To the solution 35.0 g (329 mmol) of lithium perchlorate and 33.4 g (547 mmol) of 2-aminoethanol were added. The mixture was heated under reflux for 16 hours. After cooling to room temperature, the reaction mixture was diluted with ethyl acetate and washed with a saturated aqueous solution of sodium chloride and dried over anhydrous sodium sulfate, and the solvent was distilled off under reduced pressure to give a residue which was dissolved in 700 ml of methylene chloride. To the solution, 22.8 ml (164 mmol) of triethylamine and 26.3 g (120 mmol) of di-tert-butyl dicarbonate were added. The mixture was stirred at room temperature for 12 hours. The reaction mixture was poured into water and the mixture was extracted with methylene chloride. The organic layer was washed with a saturated aqueous solution of sodium chloride and dried over anhydrous sodium sulfate, and the solvent was distilled off under reduced pressure to give a residue which was purified by column chromatography over silica gel (eluting solvent: n-hexane: ethyl acetate=4:1 to 7:3), whereby 49.9 g of the title compound were obtained.

$[\alpha]_D^{24}$:+3.92 (c=0.72, methanol); Nuclear magnetic resonance spectrum (400 MHz, CDCl$_3$) δ ppm: 7.30–7.75 (3H, m), 5.30 and 5.57 (total 1H, each br.s), 3.05–4.00 (9H, m), 2.00–2.40 (2H, m), 1.53 (9H, s), 0.94 (9H, s), 0.09 (3H, s), 0.07 (3H, s). Infrared absorption spectrum: $v_{max}$ cm$^{-1}$ (KBr): 3420, 2957, 2933, 2885, 2861, 1687; Mass spectrum (FAB) m/z: 508 ((M+H)$^+$).

[Referential Example 6(c)]

2-[4-tert-Butoxycarbonyl-(2R)-(3,4-dichlorophenyl) morpholin-2-yl]ethanol tert-butyldimethylsilyl ether In 600 ml of dried toluene, 49.9 g (98.1 mmol) of the 4-(tert-butyldimethylsilyloxy)-(2R)-(3,4-dichlorophenyl)-1-[N-(tert-butoxycarbonyl)-N-(2-hydroxyethyl)amino]-2-butanol obtained in Referential Example 6(b) and 30.9 g (118 mmol) of triphenylphosphine were dissolved. To the solution, 51.3 g (118 mmol) of a 40% solution of diethyl azodicarboxylate in toluene were added dropwise at room temperature under an atmosphere of nitrogen, followed by stirring for 2 hours. The solvent of the reaction mixture was distilled off under reduced pressure to afford a residue, which was purified by column chromatography over silica gel (eluting solvent: n-hexane: ethyl acetate=47:3 to 23:2), whereby 43.2 g of the title compound were obtained.

$[\alpha]_D^{24}$:+32.67 (c=0.60, methanol); Nuclear magnetic resonance spectrum (400 MHz, CDCl$_3$) δ ppm: 7.56 (1H, br.s), 7.43 (1H, d, J=9 Hz), 7.28 (1H, dd, J=2.9 Hz), 3.00–4.55 (8H, m), 1.80–2.10 (2H, m), 1.35–1.60 (9H, br.s), 0.85 (9H, s), −0.01 (6H, s). Infrared absorption spectrum: $v_{max}$ cm$^{-1}$ (CHCl$_3$): 2957, 2931, 2859, 1687; Mass spectrum (FAB) m/z: 490 ((M+H)$^+$).

[Referential Example 6(d)]

(2R)-(3,4-Dichlorophenyly-2-(2-hydroxyethylymorpholine hydrochloride

In 600 ml of a 4N solution of hydrogen chloride in dioxane, 43.1 g (87.9 mmol) of 2-[4-tert-butoxycarbonyl-(2R)-(3,4-dichlorophenyl)morpholin-2-yl]ethanol tert-butyldimethylsilyl ether obtained in Referential Example 6(c) were dissolved. The resulting solution was stirred at 60° C. for 4 hours. After the solvent of the reaction mixture was distilled off under reduced pressure, diethyl ether was added to the residue. The solvent of the mixture was distilled off under reduced pressure to give a residue, which was recrystallized from ethanol/ethyl acetate, whereby 24.1 g of the title compound were obtained.

$[\alpha]_D^{24}$:+48.07 (c=0.57, methanol); Nuclear magnetic resonance spectrum (400 MHz, DMSO-d$_6$) δ ppm: 8.60–9.80 (2H, br.s), 7.72 (1H, s), 7.70 (1H, d, J=9 Hz), 7.44 (1H, dd, J=2, 9 Hz), 4.53 (1H, br.s), 3.89 (1H, dt, J=4, 13 Hz), 3.75 (1H, d, J=14 Hz), 3.68 (1H, m), 3.30–3.45 (2H,m), 2.93–3.13 (3H, m), 2.09 (1H, m), 1.90 (1H, m). Infrared absorption spectrum: $v_{max}$ cm$^{-1}$ (KBr): 3378, 2966, 2893, 2812, 2783, 2724, 2656, 2530, 1598; Mass spectrum (FAB) m/z: 276 ((M+H)$^+$ free form)).

[Referential Example 6(e)]

2-[(2R)-(3,4-Dichlorophenyl)-4-(3,4,5-trimethoxybenzoyl)morpholin-2-yl]ethanol

In 500 ml of methylene chloride, 22.9 g (82.9 mmol) of the (2R)-(3,4-dichlorophenyl)-2-(2-hydroxyethyl)morpholine hydrochloride obtained in Referential Example 6(d) were suspended. To the suspension, 27.6 ml (1.99 mmol) of triethylamine, 21.0 g (91.0 mmol) of 3,4,5-trimethoxybenzoyl chloride and 100 mg of 4-dimethylaminopyridine were added, followed by stirring at room temperature for 12 hours. The reaction mixture was poured into water and the mixture was extracted with methylene chloride. The organic layer was washed with a saturated aqueous solution of sodium chloride and dried over anhydrous sodium sulfate, and the solvent was distilled off under reduced pressure to give a residue, which was purified by column chromatography over silica gel (eluting solvent: methylene chloride: acetone=4:1 to 7:3), whereby 30.0 g of the title compound were obtained.

$[\alpha]_D^{24}$:+30.65 (c=0.56, methanol); Nuclear magnetic resonance spectrum (400 MHz, CDCl$_3$) δ ppm: 6.80–7.80 (3H, m), 6.47 (2H, s), 3.40–4.80 (8H, m), 3.84 and 3.86 (total 9H, s each), 1.75–2.25 (2H, m); Infrared absorption spectrum: $v_{max}$ cm$^{-1}$ (KBr): 3429, 2940, 2838, 1630, 1585; Mass spectrum (EI) m/z: 469 (M$^+$).

[Referential Example 6(f)]

2-[(2R)-(3,4-Dichlorophenyl)-4-(3,4,5-trimethoxybenzoyl)morpholin-2-yl]ethanol methanesulfonate In 500 ml of methylene chloride, 30.0 g (63.8 mmol) of 2-[(2R)-(3,4-dichlorophenyl)4-(3,4,5-trimethoxybenzoyl)morpholin-2-yl]ethanol obtained in Referential Example 6(e) were dissolved, followed by successive addition of 11.5 ml (83.0 mmol) of triethylamine and 5.93 ml (76.6 mmol) of methanesulfonyl chloride under ice-cooling. Under an atmosphere of nitrogen, the mixture was stirred at room temperature for 2 hours. The reaction mixture was diluted with methylene chloride, washed with 1N hydrochloric acid and a saturated aqueous solution of sodium chloride and then dried over anhydrous sodium sulfate. The solvent was distilled off under reduced pressure to give a residue. The residue was purified by chromatography on a silica gel column (eluting solvent: n-hexane: ethyl acetate=1:4 to 1:9), whereby 34.8 g of the title compound were obtained.

$[\alpha]_D^{24}$:+26.36 (c=0.66, methanol); Nuclear magnetic resonance spectrum (400 MHz, CDCl$_3$) δ ppm: 6.90–7.80 (3H,m), 6.52 (2H s), 3.40–4.35 (8H, m), 3.86 and 3.87 (total 9H, s each), 2.93 (3H, s), 2.10–2.55 (2H, m).

Infrared absorption spectrum: $v_{max}$ cm$^{-1}$ (KBr): 2999, 2966, 2939, 2875, 1634, 1585; Mass spectrum (FAB) m/z: 548((M+H)$^+$).

[Referential Example 6(g)]

1-{2-[(2R)-(3,4-Dichlorophenyl)4-(3,4,5-trimethoxybenzoyl)morpholin-2-yl]ethyl}-spiro[benzo[c]thiophene-1(3H),4'-piperidin]-(2S)-oxide In 150 ml of anhydrous dimethylformamide, 15.00 g (27.4 mmol) of the mesylated compound obtained in Referential Example 6(f), 7.76 g (30.1 mmol) of spiro[benzo

[c]thiophene-1(3H),4'-piperidin]-(2S)-oxide hydrochloride, 6.89 g (82.0 mmol) of sodium bicarbonate and 6.81 g (41.0 mmol) of potassium iodide were suspended, followed by heating at 80° C. for 8 hours under an atmosphere of nitrogen. The reaction mixture was poured into 400 ml of a saturated aqueous solution of sodium chloride and extracted with ethyl acetate. The organic layer was dried over anhydrous magnesium sulfate and then the solvent was distilled off under reduced pressure to afford a residue. The residue was purified by chromatography on a silica gel column (eluting solvent: methylene chloride: methanol=40:1 to 20:1), followed by crystallization from n-hexane, whereby 15.5 g of the title compound were obtained as white crystals. $[\alpha]_D^{24}$:+14.0 (c=1, methanol); HPLC analysis: Column: YMC-Pack ODS-A (250 ×4.6 mm$\phi$); Eluting solvent: $CH_3CN$: $H_2O$=40:60, 0.1% ammonium acetate; Flow rate: 1.0 min/min; Retention time: 23.7 min.

Nuclear magnetic resonance spectrum (400 MHz, $CDCl_3$) δ ppm: 7.1–7.8 (7H, m), 6.49 (2H, br.s), 4.31 (1H, d, J=16.8 Hz), 3.99 (1H, d, J=16.8 Hz), 3.86 and 3.84 (total 9H, s each), 3.3–4.0 (6H, m), 1.5–3.1 (12H, m); Infrared absorption spectrum: $v_{max\ cm}^{-1}$ (KBr): 2939, 1636, 1584, 1464, 1426, 1329, 1237, 1128; Mass spectrum (FAB) m/z: 673 ((M+H)$^+$); Elementary analysis (for $C_{34}H_{38}N_2O_6SCl_2 \cdot 0.5H_2O$ (%)); Calculated: C: 59.82, H: 5.76, N: 4.10, S: 4.70, Cl: 10.39; Found: C: 60.20, H: 6.14, N: 4.04, S: 4.54, Cl: 10.38.

Referential Example 7

1-{2-[(2R)-(3,4-Dichlorophenyl)4-(3,4,5-trimethoxybenzoyl)morpholin-2-yl]ethyl}spiro[benzo[c]thiophene-1(3H),4'-piperidin]-(2S)-oxide

[Referential Example 7(a)]

2-[(2R)-(3,4-Dichlorophenyl)4-(3,4,5-trimethoxybenzoyl)morpholin-2-yl]ethanal

In 10 ml of methylene chloride, 0.88 ml (10.1 mmol) of oxalyl chloride were dissolved. To the resulting solution, a solution of 0.79 ml (11.1 mmol) of dimethylsulfoxide in methylene chloride (5 ml) was added dropwise at −78° C. under an atmosphere of nitrogen, followed by stirring for 30 minutes. To the reaction mixture, a solution of 950 mg (2.02 mmol) of 2-[(2R)-(3,4-dichlorophenyl)-4-(3,4,5-trimethoxybenzoyl)morpholin-2-yl]ethanol obtained in Referential Example 6(e) in methylene chloride (10 ml) was added dropwise and the mixture was stirred for 4 hours. To the reaction mixture, 2.24 ml (16.2 mmol) of triethylamine were added, followed by stirring at room temperature for 2 hours. The reaction mixture was poured into water and extracted with methylene chloride. The organic layer was washed with water and a saturated aqueous solution of sodium chloride and dried over anhydrous sodium sulfate, and the solvent was distilled off under reduced pressure to give a residue. The residue was purified by chromatography on a silica gel column (eluting solvent: methylene chloride: acetone=23:2 to 21:4), whereby 878 mg of the title compound were obtained.

$[\alpha]_D^{24}$:+36.15 (c=0.65, methanol); Nuclear magnetic resonance spectrum (400 MHz, $CDCl_3$) δ ppm: 9.56 (1H,s), 6.90–7.80 (3H, m), 6.50 (2H, s), 3.40–4.60 (6H m), 3.85–3.87 (total 9H, s each), 2.70–3.05 (2H, m); Infrared absorption spectrum: $v_{max}$ cm$^{-1}$ (KBr): 2962, 2930, 2838, 1723, 1636, 1585; Mass spectrum (FAB) m/z: 468 ((M+H)$^+$).

[Referential Example 7(b)]

1-{2-[(2R)-(3,4-Dichlorophenyl)-4-( 3,4,5-trimethoxybenzoyl)morpholin-2-yl]ethyl}spiro[benzo[c]thiophene-1(3H),4'-piperidin]-(2S)-oxide In 1 ml of methanol, 150 mg (0.32 mmol) of the 2-[(2R)-(3,4-dichlorophenyl)4-(3,4,5-trimethoxybenzoyl)morpholin-2-yl]ethanal obtained in Referential Example 7(a) and 99 mg (0.38 mmol) of spiro[benzo[c]thiophene-1(3H),4'-piperidin]-(2S)-oxide hydrochloride were dissolved. To the resulting solution, 100 mg of Molecular sieves 3A (powder) and 209 mg (3.33 mmol) of sodium cyanoborohydride were added, followed by heating under reflux for 8 hours under an atmosphere of nitrogen. The reaction mixture was filtered through Celite. The filtrate was poured into water and extracted with ethyl acetate. The organic layer was washed with a saturated aqueous solution of sodium chloride and dried over anhydrous sodium sulfate, and the solvent was distilled off under reduced pressure to afford a residue. The residue was purified by chromatography on a silica gel column (eluting solvent: methylene chloride: methanol=97:3 to 19:1), whereby 184 mg of the title compound were obtained. Spectral data of this product were identical to those of the compound prepared in Referential Example 6.

Test 1

Inhibitory Effect Against Increased Vascular Permeability

The inhibitory effect on increased vascular permeability induced by substance P (SP), an $NK_1$ receptor agonist, was assessed based on the amount of pigment leakage as an index using guinea pigs (body weight: approx. 400 g, male Hartley guinea pigs).

A pigment (Evans blue: 40 mg/kg) was administered to the femoral vein of a guinea pig anesthetized with pentobarbital (30 mg/kg, i.p.) and immediately after that, SP (1 μg/kg) was intravenously injected to induce accentuation of vascular permeability. Fifteen minutes after the injection, the guinea pig was sacrificed under anesthesia with chloroform and the amount of the pigment leaked into the primary bronchus site was measured in accordance with Harada's method (J. Pharm. Pharmacol. 23, 218(1971)). A test substance was suspended in a 0.5% tragacanth suspension and orally administered to a guinea pig 1 hour before induction by SP. Its inhibitory action was determined by the ratio of the pigment leaked from the test-substance-administered group to that from the non-administered group. In Table 1, 50% inhibitory dose ($ID_{50}$) and inhibitory rate in the case of oral administration at 3.3 mg/kg are shown.

TABLE 1

| Test substance | ID50 (mg/kg, p.o.) | Inhibitory rate (%) on oral administration at 3.3 mg/kg |
|---|---|---|
| Compound of Ex. 1 | 5.1 | 48.0 |
| Compound of Ex. 2 | — | 46.8 |
| Compound A | greater than 10 | — |
| Compound C | — | 44.1 |

The compounds of the present invention exhibited equivalent activity to that of Compound C of the prior art in the in vivo antagonism test against $NK_1$ receptor.

Test 2

Inhibitory Effect Against Bronchoconstriction

The inhibitory effect on bronchoconstriction induced with [Nle$^{10}$]-NKA[4-10], an $NK_2$ receptor agonist, was assessed based on airway pressure as an index according to the modified method of Konzett-Roessler [Naunyn-Schmiedebergs Arch. Exp. Pathol. Pharmakol. 195, 71(1940)] using guinea pigs (body weight: approximately 500 g, male Hartley guinea pigs).

Immediately after canulating the trachea of the guinea pigs under pentobarbital anaesthesia (30 mg/kg, s.c.) and treatment with gallamine (20 mg/kg, i.v.), the animals were ventilated artificially with a constant volume respiration pump (Ugo-Basile, 7025) at a frequency of 60 per minute and a tidal volume of 8 ml/kg. Airway pressure during artificial respiration was amplified by means of a pressure transducer (Nihon Koden, TP-200T) installed in a branch of the trachea cannula, detected (Nihon Koden, AP-610G), and recorded with a recorder (Nihon Koden, WT-685G). Five minutes after pre-treatment with atropine (1 mg/kg, i.v.) and propranolol (1 mg/kg, i.v.), 4 μg/kg of [Nle$^{10}$]-NKA[4-10] was intravenously administered to induce bronchoconstriction and then the pressure in the airway was measured for 10 minutes. A test substance was prepared in a similar manner to that described in Test 1 and orally administered one hour before induction with [Nle$^{10}$]-NKA[4-10]. The inhibitory effect was determined by the area under the curve of the airway internal pressure of a group administered a test substance and that of a non-administered group. In Table 2, 50% inhibitory dose (ID$_{50}$) is shown.

(When Compound A was subjected to a test by intravenous injection prior to the above-described oral administration test, it exhibited ID$_{50}$ of greater than 10 mg/kg. Therefore no oral administration test was conducted on it.)

TABLE 2

| Test medicament | ID$_{50}$ (mg/kg, p.o.) |
|---|---|
| Compound of Ex. 1 | 0.51 |
| Compound of Ex. 2 | 0.54 |
| Compound C | 35 |

The compounds according to the present invention exhibited markedly superior activity to the compound of the prior art in the in vivo test of antagonistic effect against NK$_2$ receptor.

As is apparent from Tables 1 and 2, the compounds according to the present invention exhibited excellent antagonistic action against both an NK$_1$ receptor and an NK$_2$ receptor. Described specifically, the compounds exhibited antagonistic action against an NK$_1$ receptor at the same level as the compounds of the prior art and exhibited antagonistic action against an NK$_2$ receptor superior to that of the compounds of the prior art.

Formulation Example 1
Powders

Powders can be obtained by mixing 5 g of the compound of Example 1, 895 g of lactose and 10 g of corn starch in a blender. The powders contain the compound of Example 1 in an amount of 5 mg/g.

Formulation Example 2
Granules

After 5 g of the compound of Example 1, 865 g of lactose and 100 g of low-substituted hydroxypropylcellulose are mixed, 300 g of a 10% aqueous solution of hydroxypropylcellulose are added to the resulting mixture, followed by kneading. Granules can be obtained by granulating the kneaded mass in an extrusion granulator and drying the resulting granules. The resulting granules contain the compound of Example 1 in an amount of 5 mg/g.

Formulation Example 3
Capsules

Capsules can be obtained by mixing 5 g of the compound of Example 1, 115 g of lactose, 58 g of corn starch and 2 g of magnesium stearate in a V-shaped mixer and then filling a No. 3 capsule with a 180 mg portion of the resulting mixture. Each capsule contains 5 mg of the compound of Example 1.

Formulation Example 4
Tablets

Tablets can be obtained by mixing 5 g of the compound of Example 1, 90 g of lactose, 34 g of corn starch, 20 g of crystalline cellulose and 1 g of magnesium stearate in a blender and then tableting the resulting mixture on a tableting machine.

The novel salts of the optically active sulfoxide derivative according to the present invention exhibit excellent antagonistic action against both substance P receptors and neurokinin A receptors and in addition, have low toxicity so that they are useful as a preventive agent or remedy for tachykinin-mediated diseases.

We claim:

1. A compound selected from the group consisting of the hydrochloride and the fumarate of 1-{2-[(2R)-(3,4dichlorophenyl)-4(3,4,5-trimethoxybenzoyl)morpholin-2-yl]ethyl}spiro[benzo(c)thiophene-1(3H),4'-piperidin]-(2S)-oxide.

2. The hydrochloride of 1-{2-[(2R)-(3,4-dichlorophenyl) 4-(3,4,5-trimethoxybenzoyl)morpholin-2-yl]ethyl}spiro [benzo(c)thiophene-1(3H),4'-piperidin]-(2S)-oxide.

3. The fumarate of 1-{2-[(2R)-(3,4-dichlorophenyl)-4-(3, 4,5-trimethoxybenzoyl)morpholin-2-yl]ethyl}spiro[benzo (c)thiophene-1(3H),4'-piperidin]-(2S)-oxide.

4. A pharmaceutical composition comprising a pharmaceutically acceptable diluent or carrier in combination with a pharmacologically effective amount of a compound according to claim 1 as an active ingredient.

5. A pharmaceutical composition comprising a pharmaceutically acceptable diluent or carrier in combination with a pharmacologically effective amount of a compound according to claim 2 as an active ingredient.

6. A pharmaceutical composition comprising a pharmaceutically acceptable diluent or carrier in combination with a pharmacologically effective amount of a compound according to claim 3 as an active ingredient.

7. A method for prophylaxis or treatment of tachykinin-mediated diseases, which comprises administering a pharmacologically effective amount of a compound according to claim 1 to a warm-blooded animal.

8. A method for prophylaxis or treatment of tachykinin-mediated diseases, which comprises administering a pharmacologically effective amount of a compound according to claim 2 to a warm-blooded animal.

9. A method for prophylaxis or treatment of tachykinin-mediated diseases, which comprises administering a pharmacologically effective amount of a compound according to claim 3 to a warm-blooded animal.

10. A method for inhibiting an NK$_1$ receptor and/or an NK$_2$ receptor, which comprises administering a pharmacologically effective amount of a compound according to claim 1 to a warm-blooded animal.

11. A method for inhibiting an NK$_1$ receptor and/or an NK$_2$ receptor, which comprises administering a pharmacologically effective amount of a compound according to claim 2 to a warm-blooded animal.

12. A method for inhibiting an NK$_1$ receptor and/or an NK$_2$ receptor, which comprises administering a pharmacologically effective amount of a compound according to claim 3 to a warm-blooded animal.

13. A method for prophylaxis or treatment of asthma and/or bronchitis, which comprises administering a pharmacologically effective amount of a compound according to claim 1 to a warm-blooded animal.

14. A method for prophylaxis or treatment of asthma and/or bronchitis, which comprises administering a pharmacologically effective amount of a compound according to claim 2 to a warm-blooded animal.

15. A method for prophylaxis or treatment of asthma and/or bronchitis, which comprises administering a pharmacologically effective amount of a compound according to claim 3 to a warm-blooded animal.

16. A method for prophylaxis or treatment of rhinitis, which comprises administering a pharmacologically effective amount of a compound according to claim 1 to a warm-blooded animal.

17. A method for prophylaxis or treatment of rhinitis, which comprises administering a pharmacologically effective amount of a compound according to claim 2 to a warm-blooded animal.

18. A method for prophylaxis or treatment of rhinitis, which comprises administering a pharmacologically effective amount of a compound according to claim 3 to a warm-blooded animal.

19. A method for prophylaxis or treatment of allergy, which comprises administering a pharmacologically effective amount of a compound according to claim 1 to a warm-blooded animal.

20. A method for prophylaxis or treatment of allergy, which comprises administering a pharmacologically effective amount of a compound according to claim 2 to a warm-blooded animal.

21. A method for prophylaxis or treatment of allergy, which comprises administering a pharmacologically effective amount of a compound according to claim 3 to a warm-blooded animal.

22. A method for prophylaxis or treatment of urinary incontinence, which comprises administering a pharmacologically effective amount of a compound according to claim 1 to a warm-blooded animal.

23. A method for prophylaxis or treatment of urinary incontinence, which comprises administering a pharmacologically effective amount of a compound according to claim 2 to a warm-blooded animal.

24. A method for prophylaxis or treatment of urinary incontinence, which comprises administering a pharmacologically effective amount of a compound according to claim 3 to a warm-blooded animal.

25. A method for prophylaxis or treatment of ulcerative colitis, which comprises administering a pharmacologically effective amount of a compound according to claim 1 to a warm-blooded animal.

26. A method for prophylaxis or treatment of ulcerative colitis, which comprises administering a pharmacologically effective amount of a compound according to claim 2 to a warm-blooded animal.

27. A method for prophylaxis or treatment of ulcerative colitis, which comprises administering a pharmacologically effective amount of a compound according to claim 3 to a warm-blooded animal.

* * * * *